United States Patent [19]

Morton et al.

[11] Patent Number: 4,528,181

[45] Date of Patent: Jul. 9, 1985

[54] DENTIFRICE CONTAINING DUAL SOURCES OF FLUORIDE

[75] Inventors: Anthony J. Morton, Ashton-under-Lyne; Kenneth Harvey, Wilmslow; Harry Hayes, Thelwall, all of England

[73] Assignee: Colgate-Palmolive Company, New York, N.Y.

[21] Appl. No.: 576,046

[22] Filed: Feb. 1, 1984

[51] Int. Cl.$^3$ .................... A61K 9/161; A61K 9/18
[52] U.S. Cl. ........................ 424/52; 424/49
[58] Field of Search ........................ 424/52

[56] References Cited

U.S. PATENT DOCUMENTS

| | | | |
|---|---|---|---|
| 3,932,606 | 1/1976 | Barth et al. | 424/52 |
| 3,934,002 | 1/1976 | Haefele | 424/54 |
| 3,939,261 | 2/1976 | Barth | 424/52 |
| 4,141,969 | 2/1979 | Mitchell | 424/52 |
| 4,159,280 | 6/1979 | Wason | 206/524.4 |
| 4,193,988 | 3/1980 | Forward et al. | 424/52 |
| 4,259,316 | 3/1981 | Nakashima et al. | 424/52 |
| 4,263,276 | 4/1981 | Harvey | 424/52 |
| 4,305,928 | 12/1981 | Harvey | 424/52 |
| 4,332,791 | 6/1982 | Raaf et al. | 424/52 |
| 4,335,102 | 6/1982 | Nakashima et al. | 424/52 |
| 4,339,429 | 7/1982 | Raaf et al. | 424/52 |
| 4,340,584 | 7/1982 | Wason | 424/52 |

FOREIGN PATENT DOCUMENTS

| | | |
|---|---|---|
| 56-18913 | 2/1981 | Japan . |
| 56-18911 | 2/1981 | Japan . |
| 56-22721 | 3/1981 | Japan . |
| 56-39008 | 4/1981 | Japan . |
| 56-45408 | 4/1981 | Japan . |
| 56-75422 | 6/1981 | Japan . |
| 1408922 | 10/1975 | United Kingdom . |
| 2038303 | 7/1980 | United Kingdom . |

*Primary Examiner*—Shep K. Rose
*Attorney, Agent, or Firm*—Robert L. Stone; Murray M. Grill; Herbert S. Sylvester

[57] ABSTRACT

Dentifrice containing a liquid vehicle containing water, a gelling agent, a dual source of at least about 500 ppm of fluorine comprising sodium fluoride and sodium monofluorophosphate, a precipitated, amorphous silica gel having an average particle size of 1 to 30 microns and (a) a surface area of 1 to 600 m$^2$/g,
(b) a pore volume of 0.05 to 0.5 cm$^3$/g,
(c) a product of surface area (in m$^2$/g) × pore volume (in cm$^3$/g) less than or equal to 240,
(d) a calculated pore diameter of 1.5 to 2.5 nm, and
(e) a water content of less than 25% by weight, a source of calcium corresponding to up to about 0.004% by weight (40 ppm) of calcium ion and about 0.25%–5% by weight of an alkali metal phytate. The alkali metal phytate improves retention of total soluble fluorine.

9 Claims, No Drawings

DENTIFRICE CONTAINING DUAL SOURCES OF FLUORIDE

This invention relates to a dentifrice containing dual sources of flourine. In particular it relates to dentifrices containing a synthetic, precipitated amorphous silica gel and dual sources of fluorine in which high levels of soluble fluorine are retained in the dentifrice. Further, the dentifrices may be compatibly stable in an unlined (or unlacquered) aluminium tube.

The synthetic, precipitated, amorphous silica gel polishing agent employed in the present invention has been particularly described in British Published Patent Application No. 2 038 303A of Grace G.m.b.H., which is incorporated herein by reference. The water content of this silica gel (up to about 25% by weight) is present in hydrogel form. The silica gel is generally described as having an average particle size of 1 to 30 microns and (a) a surface area of 1 to 600 $m^2/g$,
(b) a pore volume of 0.05 to 0.5 $cm^3/g$,
(c) a product of surface area (in $m^2/g$) x pore volume (in $cm^3/g$) less than or equal to 240,
(d) a calculated pore diameter of 1.5 to 2.5 nm, and
(e) a water content of less than 25% by weight.

In U.S. Pat. Nos. 4,141,969 to Mitchell and 4,159,280 to Wason, dentifrices are described in which calcium ion in amount above 0.01% or 0.005% by weight effects compatibility of the dentifrices with an unlined aluminium tube surface when a source of fluorine from a fluorine providing compound such as sodium monofluorophosphate and siliceous polishing agent is present. It has been found that when dual fluorine sources, particularly a mixture of sodium fluoride and sodium monofluorophosphate from separate sources (i.e. sodium fluoride is present in addition to that inherently contained in commercial grades of sodium monofluorophosphate), synthetic, precipitated amorphous silica gel described in British Published Patent Application No. 2 038 303A and but small amount of calcium (e.g. up to about 0.004%, say about 0.001–0.004%), that total soluble fluoride retention is markedly diminished, perhaps due to availability of calcium ion to react with fluoride ion to form insoluble calcium fluoride.

Moreover, compatibility with unlined aluminium surface of dentifrices containing various grades of siliceous polishing agent, fluorine source and calcium may vary.

Sodium phytate is employed in the present invention to improve total soluble fluorine retention. Phytic acid and/or salt thereof, such as sodium phytate have been taught in prior art dentifrices but not to improve total soluble fluorine retention, particularly in the presence of a dual fluorine source and a siliceous polishing agent, especially the silica gel employed herein, in which total soluble fluorine retention has been diminished by the presence of calcium.

Patent disclosures which describe dentifrices containing phytic acid or salts thereof with various dentifrice ingredients, but without teaching or suggesting the present invention include:

(1) U.S. Pat. No. 3,934,002 to Haefele;
(2) U.S. Pat. No. 4,193,988 to Forward et al (British Priorities 12099/71 and 58064/71);
(3) U.S. Pat. No. 4,259,316 to Nakashima et al (Japanese Priority 54-97627);
(4) U.S. Pat. No. 4,305,928 to Harvey (British Priority 20759/78);
(5) U.S. Pat. No. 4,335,102 to Nakashima et al (Japanese Priority 54-121194);
(6) British Pat. No. 1,408,922 to Raaf et al;
(7) Japanese Disclosure 18913/1981 to Lion (Application 54-94625);
(8) Japanese Disclosure 18911/1981 to Lion (Application 54-94626);
(9) Japanese Disclosure 22721/1981 to Lion (Application 54-97628);
(10) Japanese Disclosure 39008/1981 to Lion (Application 54-113773);
(11) Japanese Disclosure 45408/1981 to Lion (Application 54-121195);
(12) Japanese Disclosure 75422/1981 to Lion (Application 54-150880).

It is an advantage of this invention that a dentifrice is provided having high soluble fluorine retention.

It is a further advantage of this invention that the dentifrice thereof is compatible with an unlined aluminium tube. Further advantages will be apparent from consideration of the following specification.

In accordance with certain of its aspects this invention relates to a dentifrice comprising a liquid vehicle containing water in amount of at least about 22.5% by weight of said dentifrice, about 0.2–10% by weight of a gelling agent, a dual source of at least about 500 ppm of fluorine comprising sodium fluoride and sodium monofluorophosphate in which about 30–50% by weight of said fluorine is provided by said sodium fluoride, about 10–50% by weight of a polishing agent comprising a synthetic precipitated, amorphous silica gel having an average particle size of 1 to 30 microns and (a) a surface area of 1 to 600 $m^2/g$,
(b) a pore volume of 0.05 to 0.5 $cm^3/g$,
(c) a product of surface area (in $m^2/g$) x pore volume (in $cm^3/g$) less than or equal to 240,
(d) a calculated pore diameter of 1.5 to 2.5 nm, and
(e) a water content of less than 25% by weight, a source of calcium corresponding to up to about 0.004% by weight (40 ppm) of calcium ion in said dentifrice and about 0.25 to 5% by weight of an alkali metal phytate.

As indicated above, the synthetic precipitated silica is of the type described in British Published Patent Application No. 2 038 303A. Specific grades of the silica material described therein are suitable for use in the practice of the present invention. Further, specific grades which are particularly preferred are described in an October, 1980 trade publication of Grace G.m.b.H. of Norderstadt, Germany, as Syloblanc 81 and Syloblanc 82 as having the following typical physical and chemical characteristics:

|  | SYLOBLANC 81 | SYLOBLANC 82 |
| --- | --- | --- |
| Average particle size (according to Coulter) μm | 4 | 7 |
| Wet screen residue (42 μm) % | 0.02 | 0.02 |
| pH (5% suspension in water) | 3 | 6 |
| Surface area (B.E.T.) $m^2/g$ | 400 | 480 |
| Loss on drying % | 7 | 4 |
| $SiO_2$ content (on ignited substance) % | 96 | 99 |
| Refractive index | 1.46 | 1.46 |

Syloblanc 81, in particular, is highly effective in polishing dental surfaces. Syloblanc 82 is lower in polishing effect but can be used by consumers desiring such reduced effect. Likewise, grades of the silica material may be proportioned in mixtures to produce appropriate polishing characteristics. It is noteworthy that the dentifrices are compatible in unlined aluminium dentifrice tubes even in the absence of phytate salt.

Aqueous slurries of the silica materials (e.g. about 5 to 20% slurries) typically have a pH of about 2 to 9. Since the dentifrice composition of the present invention preferably has a pH (measured in 20% aqueous slurry) of at least about 6.5, e.g. about 6.5-9, the pH of the dentifrice may be adjusted with an appropriate material such as sodium hydroxide, sodium phosphate, etc.

The dual or binary fluorine system comprises sodium fluoride and sodium monofluorophosphate in amount to provide at least about 500 ppm of fluoride, typically about 500-10000 ppm, e.g. about 750-2000 ppm and particularly about 1000-2000 ppm, such as 1000-1670 ppm. About 30-50%, e.g. about 30-35%, by weight of the fluoride is provided by the sodium fluoride, as a separate component from the minor amount of sodium fluoride as which may inherently be present in grades of sodium monofluorophosphate. Desirably, sodium fluoride provides about 225-800 ppm of fluoride to the dentifrice.

Sodium monofluorophosphate, $Na_2PO_3F$, as commercially available, may vary considerably in purity. It may be used in any suitable purity provided that any impurities do not substantially adversely affect the desired properties. In general, the purity is desirably at least 80%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably 12.7%, a content of not more than 1.5%, preferably not more than 1.2%, of free sodium fluoride; and a sodium monofluorophosphate content of at least 12%; preferably at least 12.1% all calculated as fluoride.

The presence of a calcium salt, particularly a water-insoluble calcium salt, in amount to provide about 0.001-0.004% by weight of calcium ion to the dentifrice, markedly reduces total soluble fluorine retention unless stabilised. This could be due to formation of calcium fluoride. Typical calcium salts which are used in the dentifrice of the invention are dicalcium phosphate (dihydrate, anhydrous or mixture thereof), tricalcium phosphate, calcium pyrophosphate, calcium metasilicate, calcium carbonate, etc. In particular, dicalcium phosphate and calcium carbonate are often used.

About 0.06-0.27% by weight of dicalcium phosphate would be expected to provide to a dentifrice including water with about 0.001-0.004% of calcium ions based upon the water solubility of dicalcium phosphate at 20° C. Likewise, about 1.5-6.2% by weight of calcium carbonate would be expected to provide to a dentifrice including water about 0.001-0.004% of calcium ions.

In the present invention sodium phytate, also known as sodium inositol hexaphosphate, has been found to overcome the reduction in fluorine retention which occurs with as the dual or binary fluoride system, the described synthetic precipitated silica gel, and 0.001-0.004% by weight of calcium ion. Sodium phytate is employed in amount of about 0.1-2.5% by weight, preferably about 0.1-0.5%. When it is added to dentifrice in 40% aqueous solution, about 0.25-5% by weight, preferably about 0.5-1% of solution is employed. The pH of the dentifrice is desirably maintained at at least about 6.5, e.g. about 6.5-9, so that the phytate typically is present as salt thereof. All or up to 6 of the available phosphate groups of phytic acid have hydrogen atoms replaced by sodium atoms.

The dentifrice comprises a liquid vehicle containing about 3-60% by weight of water, typically mixed with at least one humectant. The liquid phase may comprise about 22.5-90% by weight of the dentifrice and is typically about 22.5-80% liquid, typically with about 3-50% by weight, preferably about 20-50%, of water and about 10-90% by weight, preferably about 15-80%, of humectant. Typical humectants include glycerine, sorbitol (e.g. 70% solution), polyethylene glycol of molecular weight of about 400-600, propylene glycol and mixtures thereof.

The dentifrice typically also contains a separate gelling or binding agent as a solid vehicle agent, although this may be omitted or present in small amount, since the synthetic, precipitated silica (particularly a grade such as Syloblanc 82) can effect a thickening or gelling of the dentifrice into a creamy or pasty consistency. Gelling or binding agents which may be present include sodium carboxymethyl cellulose, hydroxyethyl cellulose, hydroxypropyl cellulose, xanthan, Irish moss, gum tragacanth polyvinyl pyrrolidone, starch, water-soluble hydrophilic colloidal carboxyvinyl polymers, such as those sold as Carbopol 934 and Carbopol 940, and mixtures thereof. Such gelling agents may be used in amount of up to about 5% by weight, typically about 0.05-2% and preferably about 0.15-1.5%.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Various other materials may be incorporated in the dental creams of this invention. Examples thereof are colouring or whitening agents, preservatives, stabilizers, tetrasodium pyrophosphate, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes it may be desirable to include antibacterial agents in the compositions of the present invention. Typical antibacterial agents which may be used in amount of about 0.01% to about 5%, preferably about 0.05 to about 1.0%, by weight of the dentifrice composition include:

$N^1$-4 (chlorobenzyl) -$N^5$- (2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) 5,6-dichloro-2-guanidinobenzimidazole;
$N^1$-p-chlorophenyl-$N^5$-laurylbiguanide;
5-amino-1,3-bis (2-ethylhexyl)-5-methylhexahydropyrimidine;
and their non-toxic addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable, flavour and sweetening agents may together comprise from about 0.01 to 5% or more of the composition.

The dentifrice is typically prepared by forming a premix of the liquid vehicle components, e.g. water and humectant, which may also contain additional ingredients such as sweetener, and blending therewith the synthetic precipitated silica gel and separate gelling agent. If employed additional ingredients may then be added.

Although the invention is described with regard to illustrative examples, it will be apparent to one skilled in the art that various modifications may be made thereto which fall within its scope.

EXAMPLE 1

The following dentifrices are prepared:

| | PARTS | |
|---|---|---|
| | A | B |
| Glycerine | 25.00 | 25.00 |
| Sodium carboxymethyl cellulose | 1.20 | 1.20 |
| Sodium saccharine | 0.17 | 0.17 |
| Sodium monofluorophosphate | 0.76[1] | 0.76[1] |
| Sodium fluoride | 0.10[1] | 0.10[1] |
| Polyethylene glycol 600 | 3.00 | 3.00 |
| Silica[2] | 15.00 | 15.00 |
| Calcium carbonate | 5.00[3] | 5.00[3] |
| Phytic acid, sodium salt (40% soln) | — | 0.50 |
| Sodium lauryl sulphate | 1.50 | 1.50 |
| Flavour | 0.90 | 0.90 |
| Water | 47.37 | 46.87 |

[1] The theoretical amounts of total soluble fluorine from sodium fluoride and sodium monofluorophosphate is about 1450 ppm (0.145% of the dentifrices) about one-third of which is provided by sodium fluoride.
[2] The silica is Syloblanc 81 from Grace G.m.b.H.
[3] Corresponding to about 33 ppm of calcium.

After ageing each dentifrice in unlined and lined aluminium dentifrice tubes for 3 months at 43° C., samples of Dentifrice A reveal total soluble fluorine retention levels of 0.046% and 0.044% (460 and 440 ppm). With Dentifrice B samples aged under the same conditions reveal total soluble fluorine retention levels of 0.064% each (640 ppm), a marked improvement.

EXAMPLE 2

Dentifrices A' and B' are prepared corresponding to A and B of Example 1 except that in both A' (without phytic acid, sodium salt) and in B' (with 0.50 parts of phytic acid, sodium salt), the amount of sodium monofluorophosphate is reduced to 0.38 parts. In both A' and B', the total theoretical amounts of total soluble fluorine is about 950 ppm, about one-half being from each fluoride source.

After ageing each dentifrice in unlined and lined aluminium dentifrice tubes for 3 months at 43° C., samples of Dentifrice A' reveal total soluble fluorine retention levels of 0.016% and 0.014% (160 and 140 ppm). With Dentifrice B' samples aged under the same conditions reveal total soluble fluorine retention levels of 0.037% each (370 ppm), a marked improvement.

EXAMPLE 3

Dentifrices A" and B" are prepared corresponding to A and B of Example 1, and Dentifrices A'" and B'" are prepared corresponding to A' and B' of Example 2, except that the Syloblanc 82 from Grace G.m.b.H. is used as the synthetic precipitated, amorphous silica gel in place of Syloblanc 81.

In both Dentifrices A" and B", dentin abrasivity is lower than with A and B. Compatibility with unlined aluminium tubes is somewhat better when Syloblanc 81 is employed (Example 1).

Upon ageing for 3 months at 43° C., samples of A" (0.76 parts sodium monofluorophosphate; 0.10 parts sodium fluoride; (without phytic acid, sodium salt) have total soluble fluorine retentions of 0.063% and 0.061% (630 ppm and 610 ppm) and samples of B" (as A" but with 0.50 parts of solution of phytic acid, sodium salt) have total soluble fluorine retentions of 0.080% each (800 ppm), a marked improvement.

Upon ageing for 3 months at 43° C., samples of A'" (0.38 parts sodium monofluorophosphate; 0.10 part sodium fluoride; without phytic acid, sodium salt) have total soluble fluorine retentions of 0.023% each (230 ppm) and samples of B'" (as A'" but with 0.50 parts of solution of phytic acid, sodium salt) have total soluble fluorine retensions of 0.042% and 0.041% (420 ppm and 410 ppm), a marked improvement.

Modification of the exemplified dentifrices to employ Syloblanc 81 and Syloblanc 82 in 1:1 ratio provides desirable dentine abrasion and total soluble fluorine retention.

It will be apparent to those skilled in the art that further modifications of the examples illustrative of the invention, may be made thereto.

We claim:

1. A dentifrice comprising a liquid vehicle containing water in amount of at least about 3% by weight of said dentifrice, about 0.05–5% by weight of a gelling agent, a dual source of at least about 500 ppm of fluorine comprising sodium fluoride and sodium monofluorophosphate in which about 30–50% by weight of said fluoride is provided by said sodium fluoride, about 10–50% by weight of a polishing agent comprising a synthetic precipitated, amorphous silica gel having an average particle size of 1 to 30 microns and
(a) a surface area of 1 to 600 $m^2/g$,
(b) a pore volume of 0.05 to 0.5 $cm^3/g$,
(c) a product of surface area (in $m^2/g$) x pore volume (in $cm^3/g$ less than or equal to 240,
(d) a calculated pore diameter of 1.5 to 2.5 nm, and
(e) a water content of less than 25% by weight,
a source of calcium corresponding to an amount to provide up to about 0.004% by weight of calcium ion in said dentifrice and about 0.1 to 2.5% by weight of an alkali metal phytate.

2. The dentifrice claimed in claim 1 wherein said liquid vehicle is present in amount of about 22.5–90% by weight with water being in amount of about 3–50% by weight of the dentifrice.

3. The dentifrice claimed in claim 1 wherein said amount of fluoride is about 750–2000 ppm.

4. The dentifrice claimed in claim 1 wherein 0.76% by weight of sodium monofluorophosphate and 0.10% by weight of sodium fluoride are present.

5. The dentifrice claimed in claim 1 wherein 0.38% by weight of sodium monofluorophosphate and 0.10% of sodium fluoride are present.

6. The dentifrice claimed in claim 1 wherein said source of calcium is selected from the group consisting of dicalcium phosphate, tricalcium phosphate, calcium pyrophosphate, calcium metasilicate and calcium carbonate.

7. The dentifrice claimed in claim 2 wherein said source of calcium providing up to about 0.004% by weight of calcium ion is calcium carbonate in amount of up to about 6.2% by weight of said dentifrice.

8. The dentifrice claimed in claim 1 wherein said alkali metal phytate is sodium phytate.

9. The dentifrice claimed in claim 1 wherein said alkali metal phytate is present in amount of about 0.1–0.5% by weight.

* * * * *